United States Patent
Zierhofer et al.

(10) Patent No.: US 6,556,870 B2
(45) Date of Patent: Apr. 29, 2003

(54) PARTIALLY INSERTED COCHLEAR IMPLANT

(75) Inventors: Clemens M. Zierhofer, Kundl (AU); Erwin S. Hochmair, Axams (AU); Ingeborg J. Hochmair, Axams (AU)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 134 days.

(21) Appl. No.: 09/774,391

(22) Filed: Jan. 31, 2001

(65) Prior Publication Data

US 2001/0047193 A1 Nov. 29, 2001

Related U.S. Application Data

(60) Provisional application No. 60/179,176, filed on Jan. 31, 2000.

(51) Int. Cl.[7] .............................................. A61N 1/08
(52) U.S. Cl. ......................... 607/57; 607/137; 607/116; 607/56; 623/10
(58) Field of Search ............................. 607/55, 56, 57, 607/137; 623/10

(56) References Cited

U.S. PATENT DOCUMENTS

| | | | |
|---|---|---|---|
| 4,284,856 A | 8/1981 | Hochmair et al. | 179/107 |
| 4,357,497 A | 11/1982 | Hochmair et al. | 179/107 |
| 4,739,512 A | 4/1988 | Hartl et al. | 381/68.6 |
| 4,817,607 A | 4/1989 | Tatge | 128/419 |
| 5,558,618 A | 9/1996 | Maniglia | 600/25 |
| 5,800,336 A | 9/1998 | Ball et al. | 600/25 |
| 5,876,443 A | 3/1999 | Hochmair et al. | 623/10 |
| 6,231,604 B1 * | 5/2001 | von Ilberg | 623/10 |
| 6,308,101 B1 * | 10/2001 | Faltys et al. | 607/57 |

OTHER PUBLICATIONS

"Cochlear implants: technology for the profoundly deaf", *Measurement & Control*, vol. 26, Nov. 1963, pp. 267–270.
"Design and Fabrication of Multiwire Scala Tympani Electrodes", *Annals of the New York Academy of Sciences*, vol. 405, 1983, pp. 173–182.
"Mimicking the Human Ear", *IEEE Signal Processing Magazine*, Sep. 1998, pp. 101–130.
International Search Report dated Jun. 27, 2001 for PCT/IB01/00455.

* cited by examiner

Primary Examiner—Ira S. Lazarus
Assistant Examiner—Kathryn S. O'Malley
(74) Attorney, Agent, or Firm—Bromberg & Sunstein LLP

(57) ABSTRACT

A cochlear implant system has a signal processor that fits in the ear canal of a user. The signal processor processes an acoustic signal present in the ear of the user to produce a representative radio signal. A power transmitter transmits an electrical power signal through the skin of the user. A cochlear implant receives the radio signal and the electrical power signal and produces for the auditory nerve of the user an electrical stimulation signal representative of the acoustic signal.

19 Claims, 3 Drawing Sheets

PARTIALLY INSERTED COCHLEAR IMPLANT

The present application claims priority from provisional U.S. patent application No. 60/179,176, filed Jan. 31, 2000, and incorporated herein by reference.

FIELD OF THE INVENTION

The invention relates to a hearing prosthesis system using a cochlear implant.

BACKGROUND ART

Deafness may be due to total sensorineural hearing loss. This is where the cochlea does not respond to sound waves, and therefore does not generate electrical signals for transmission to the cochleal nerves. An auditory prosthesis may use a suitable stimulation electrode arrangement capable of stimulating the auditory nerves. One current prosthesis design includes an external transmitter and battery, and an internal receiver. The receiver interacts with electrodes that are surgically placed in the cochlea to allow selective stimulation of the cochlear wall (Hochmair et al., U.S. Pat. Nos. 4,284,856 and 4,357,497, incorporated herein by reference). The electrodes are typically contained in a substantially flexible electrode carrier having sufficient stiffness to be guided into the cochlea in the desired coiled shape (Hochmair-Desoyer et al., Annals of the New York Academy of Sciences 405:173-182 (1991), incorporated herein by reference).

FIG. 1 shows a section view of an ear with a typical cochlear implant system. A normal ear transmits sounds through the outer ear 10 to the eardrum 12, which moves the bones of the middle ear 14, which in turn excites the cochlea 16. The cochlea 16 includes an upper channel, known as the scala vestibuli 18, and a lower channel, known as the scala tympani 20, which are connected by the cochlear duct 22. In response to received sounds transmitted by the middle ear 14, the fluid filled scala vestibuli 18 and scala tympani 20 transmit waves, functioning as a transducer to generate electric pulses that are transmitted to the cochlear nerve 24, and ultimately to the brain.

To overcome total sensorineural hearing loss, a cochlear implant system produces direct electrical stimulation of the cochlea 16. A typical system may include an external microphone that provides an audio signal input to a signal processing stage (not shown) where various signal processing schemes can be implemented. For example, signal processing approaches that are well-known in the field of cochlear implants include continuous interleaved sampling (CIS) digital signal processing, channel specific sampling sequences (CSSS) digital signal processing (as described in co-pending U.S. patent application Ser. No. 09/648,68, filed Aug. 25, 2000, and incorporated herein by reference), spectral peak (SPEAK) digital signal processing, and compressed analog (CA) signal processing. Typically, the processed signal is then converted into a digital data format, such as a sequence of data frames, for transmission into an implanted receiver 39.

Besides getting the processed audio information to the implanted receiver 39, existing cochlear implant systems also need to deliver electrical power from outside the body through the skin to satisfy the power requirements of the implanted portion of the system. FIG. 1 shows an arrangement based on inductive coupling through the skin to transfer both the required electrical power and the processed audio information. As shown in FIG. 1, a primary coil 38 (connected to the external signal processor) is externally placed adjacent to a subcutaneous secondary coil 34 (connected to the receiver 39). This arrangement inductively couples a radio frequency (rf) electrical signal to the receiver 39.

The receiver 39 is able to extract both a power component from the rf signal it receives, and the audio information for the implanted portion of the system. Besides extracting the audio information, the receiver 39 also performs additional signal processing such as error correction, pulse formation, etc., and produces a stimulation pattern (based on the extracted audio information) that is sent through connected wires 44 to an implanted electrode carrier 46. Typically, this electrode carrier 46 includes multiple electrodes on its surface that provide selective stimulation of the cochlea 16.

The transmission rf signal for primary coil 38 is typically provided by a prominent behind-the-ear (BTE) module. This BTE module may also contain other system components such as the microphone and the external signal processing arrangement. The BTE module may be quite visually obtrusive, and it is known that some wearers of such devices are very sensitive that their appearance is abnormal.

SUMMARY OF THE INVENTION

A representative embodiment of the present device includes a signal processing device for a cochlear implant. The device body fits into the ear canal of a user. The device body includes a microphone, a signal processor, and a transmitter. The microphone converts an acoustic signal present at the device body into a representative electrical signal. The signal processor performs signal processing of the representative electrical signal to form a cochlear implant signal. The transmitter converts the cochlear implant signal into a radio signal for transmission to a cochlear implant.

Another embodiment includes a cochlear implant system that has a signal processor that fits in the ear canal of a user. The signal processor processes an acoustic signal present in the ear of the user to produce a representative radio signal. A separate power transmitter transmits an electrical power signal through the skin of the user. A cochlear implant receives the radio signal and the electrical power signal and produces for the auditory nerve of the user an electrical stimulation signal representative of the acoustic signal.

In further embodiments, the device body may include a mechanical stimulation module that delivers to the inner ear structure of the user a mechanical stimulation signal representative of a portion of the acoustic signal. In such a device the cochlear implant signal is representative of a first subrange of frequencies in the acoustic signal, and the mechanical stimulation signal is representative of a second subrange of frequencies in the acoustic signal.

The processing performed by the signal processor may include at least one of compression, beamforming, and filtering. The signal processing may be continuous interleaved sampling (CIS) digital signal processing, channel specific sampling sequences (CSSS) digital signal processing, spectral peak (SPEAK) digital signal processing, or compressed analog (CA) signal processing.

An implanted battery module may power the cochlear implant, and the battery module may be rechargeable responsive to the transmitted electrical power signal.

The cochlear implant may use extracochlear electrodes to deliver the electrical stimulation signal. Alternatively, cochleostomy window associated electrodes may deliver the electrical stimulation signal. Or, multi-channel array electrodes may be partially or fully inserted into the cochlea of the user to deliver the electrical stimulation signal.

Another embodiment includes a cochlear implant system having a power transmitter that transmits an electrical power signal through the skin of the user, and a cochlear implant. The cochlear implant includes (i) a battery module that powers the cochlear implant, and that is rechargeable responsive to the transmitted electrical power signal, and (ii) a signal processor including a microphone. The signal processor processes an acoustic signal present in the ear of the user, and produces for the auditory nerve of the user an electrical stimulation signal representative of the acoustic signal.

BRIEF DESCRIPTION OF THE DRAWINGS

The present invention will be more readily understood by reference to the following detailed description taken with the accompanying drawings, in which.

DETAILED DESCRIPTION OF SPECIFIC EMBODIMENTS

Various embodiments of the present invention are directed to a cochlear implant system that replaces the signal processing stage of the behind-the-ear (BTE) module of previous systems with an in-the-ear (ITE) module. This approach splits the power- and information-transfer functions to the implant into two independent transmission channels. Information transfer between the ITE processor and the implant uses a radio frequency (rf) connection. Power transfer uses the conventional inductively coupled coils. The transmitted power may be used to drive the implant, or implanted batteries may be recharged.

The ITE processor may be based on a conventional hearing aid, which is enhanced by an rf transmitter to communicate the audio information to the implant. Besides providing an audio signal to the implant for electrical stimulation of the auditory nerve, the ITE may also provide an acoustic mechanical stimulation module. This module can mechanically drive either the normal auditory chain of ear drum, middle ear, etc., or the round window from a cochleostomy. Such a combination of electric and mechanical auditory stimulation is described, for example, in application Ser. No. 09/258,997, filed Feb. 26, 1999, which is commonly assigned and incorporated herein by reference. Combined electric and mechanical stimulation can be particularly effective in cochlear implant patients who retain some residual hearing. Typically, the electrical stimulation provides audio information in a first range of frequencies, e.g., higher frequencies, and the mechanical stimulation provides audio information in a second range of frequencies, e.g., lower frequencies.

Figure 1:
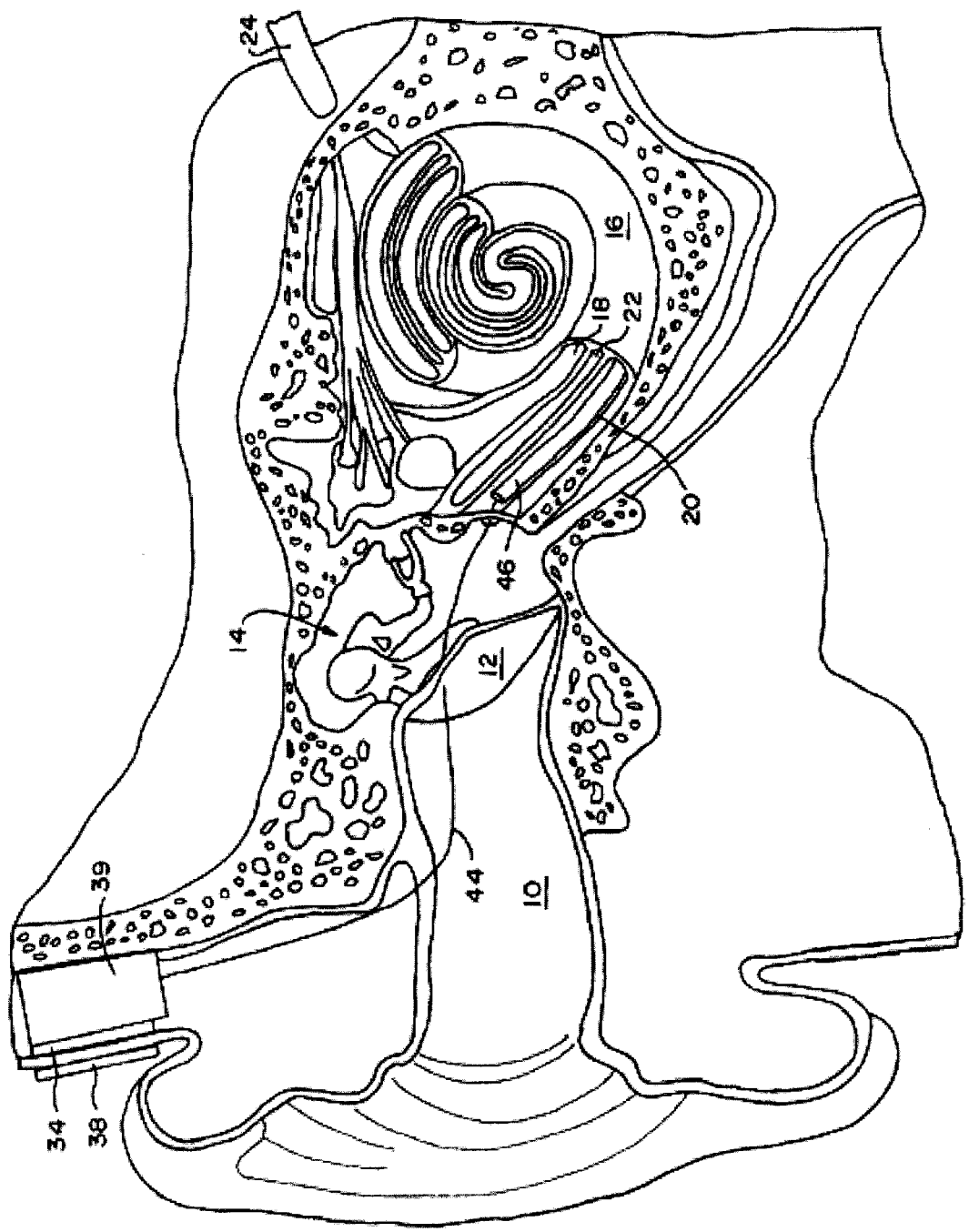
FIG. 1 illustrates a section view of an ear connected to a cochlear implant system.
Figure 2:
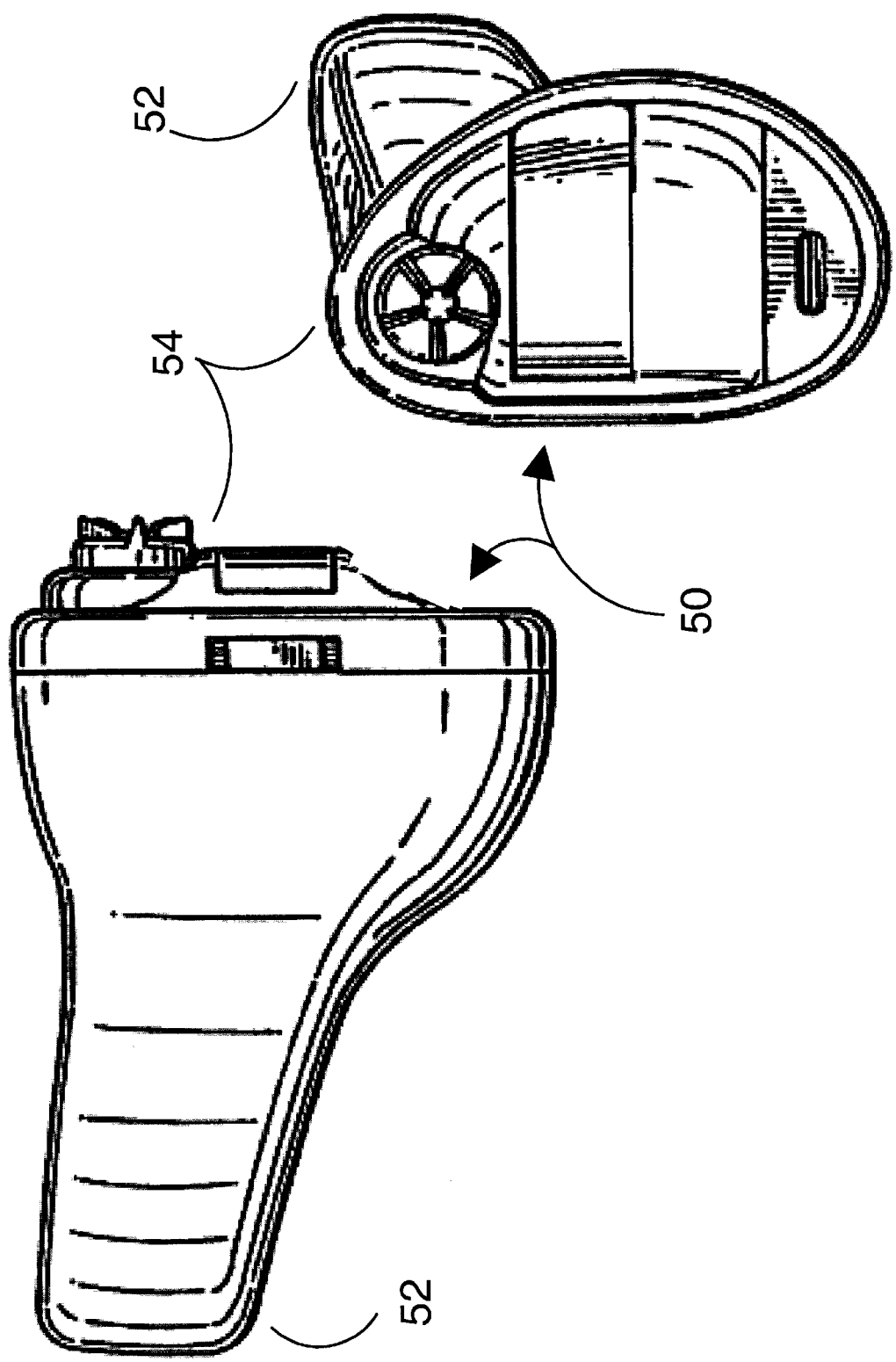
FIG. 2 shows a top and a side view of an in-the-ear processor according to one specific embodiment of the present invention.

FIG. 2 shows a top and a side view of an in-the-ear processor according to one specific embodiment of the present invention. The ITE processor 50 looks like a conventional hearing aid that is inserted into the ear canal in the outer ear, 10 in FIG. 1. A tapered inner end 52 slides into the ear canal of the outer ear 10 until it mechanically engages the eardrum 12. FIG. 2 shows the tapered inner end 52 as having a generic taper suitable for most users, but it is also known to make a custom molding of the ear canal of the outer ear 10 of the user, and to use this custom molding as the shape of the tapered inner end 52. In an embodiment having an acoustic mechanical stimulation module, the mechanical drive signal may be provided via the tapered inner end 52. Alternatively, the tapered end 52 may be adapted to mechanically drive the round window from a cochleostomy.

Figure 3:
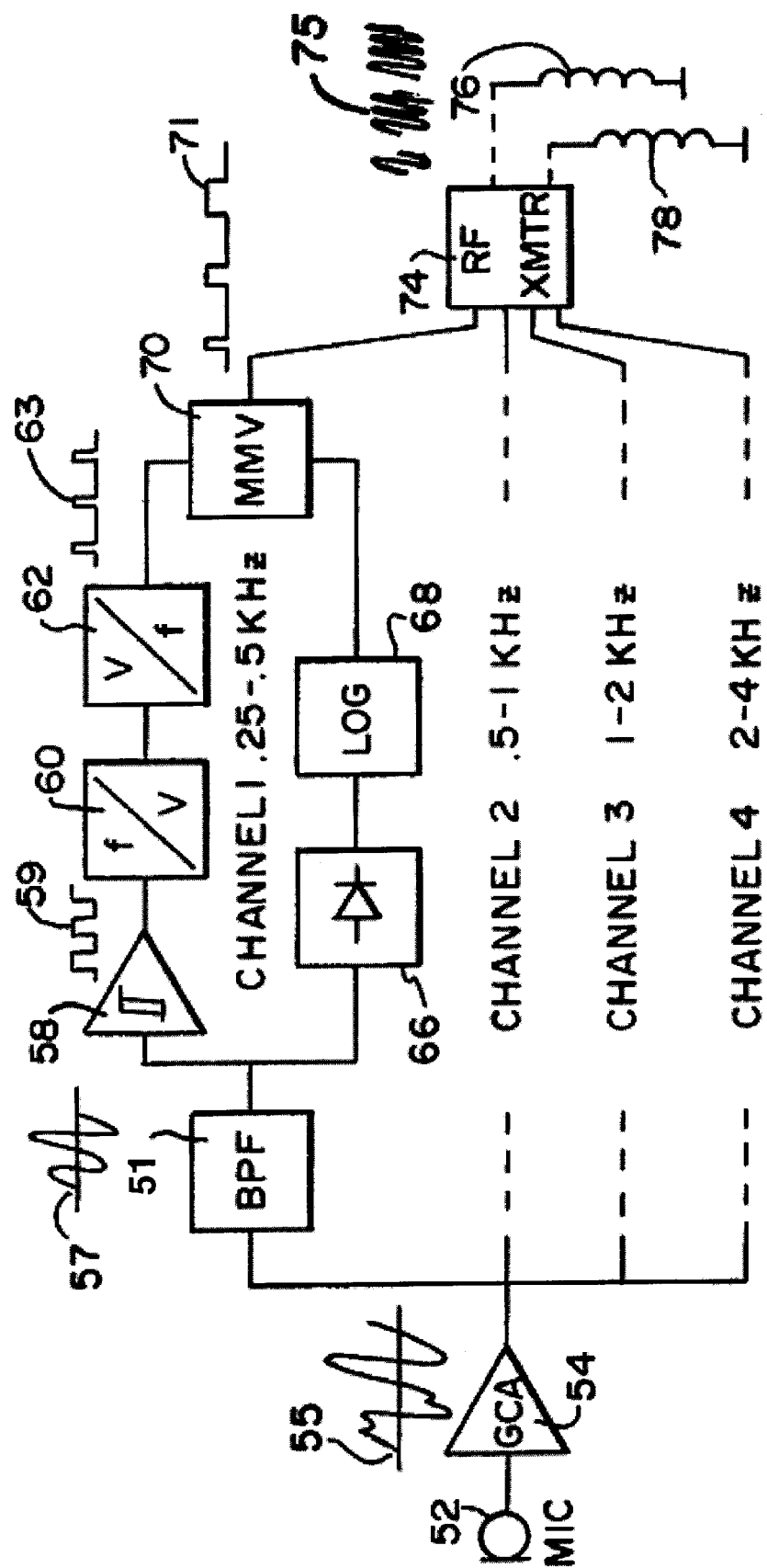
FIG. 3 shows functional blocks of an ITE processor according to one specific embodiment of the present invention.

FIG. 3 shows functional blocks of the iTE processor 50 according to one specific embodiment, which processes audio signals in the manner described in U.S. Pat. No. 4,357,497. This multi-frequency system includes four channels corresponding to four frequency bands in the audio frequency range corresponding to 0.25-0.5 Khz, 0.5-1.0 Khz, 1.0-2.0 Khz, and 2.0- 4.0 Khz. An audio signal present at the ITE processor 50 is converted in to a representative electrical signal and passed through a gain controlled amplifier 54. Signal processing circuitry for each channel includes a band pass filter 51 tuned for the desired frequency band (e.g. 0.25-0.5 Khz for channel 1). The signal from gain controlled amplifier 54 has a wide frequency range as illustrated at 55, and after passing through the band pass filter 51, a signal of limited frequency range is provided as shown at 57. Delay circuitry can be included in the lower frequency channels to compensate for the delay normally introduced in transmitting acoustic waves through the length of the cochlea for stimulating the lower frequency stimulation sites near the apex of the cochlea.

Band pass filter output signal 57 is then applied to a limiter 58, which produces a clipped output signal 59 showing the same zero-crossings as wave 57. The clipped wave 59 is applied to a frequency-to-voltage converter 60 which produces a time varying dc voltage that is proportional to the frequency of signal 59. The frequency-to-voltage converter 60 comprises suitable circuitry, such as a monostable multivibrator which is triggered by signal 59 to generate a plurality of pulses of equal pulse width and having a repetition rate corresponding to the frequency of the signal 59. The monostable multivibrator output is passed through a low pass filter to generate a time varying dc voltage which is proportional to the pulse rate.

The time varying voltage output from frequency-to-voltage converter 60 is then applied to a voltage-to-frequency converter 62 such as a voltage controlled oscillator which generates an output signal 63 comprising a train of pulses having a fixed pulse width and a frequency corresponding to the voltage applied to the voltage controlled oscillator. However, the frequency range of the pulse train 63 may vary in a limited range such as 40-400 Hz while the band-pass filter passes a smaller or larger frequency range.

The signal from band pass filter 50 is also passed through a rectifier 66 and a logarithmic amplifier 68 which produces a varying dc output voltage which is logarithmically proportional to the amplitude of the rectified signal from rectifier 66. The pulse train 63 from voltage-to-convener 62 and the voltage from logarithmic amplifier 68 are applied to a monostable multivibrator 70 which generates an output pulse train 71 whose pulse repetition rate is determined by the pulse repetition rate of pulse train 63, and whose pulse width is determined by the voltage from logarithmic amplifier 68. Output pulse train 71 is applied to an RF transmitter 74 for modulating a carrier signal, as illustrated at 75. The modulated carrier is then transmitted by antenna coil 76 or antenna coil 78.

To cooperate with the ITE processor 50, the receiver, 39 in FIG. 1, contains signal processing circuits to receive and extract the rf audio information signals from the transmitter. The extracted audio information is then processed by the receiver 39 into electrode stimulation signals, which are communicated via connecting wires 44 to the implanted electrode carrier 46 to provide electrical stimulation to the cochlea 16.

Various signal processing strategies are known in the art for stimulating the implanted electrodes in the electrode carrier 46. These include continuous interleaved sampling (CIS), channel specific sampling sequences (CSSS), spectral peak (SPEAK), and compressed analog (CA) processing. Other processing and stimulation strategies are known, and new strategies are likely to be developed in the future; these are all within the scope of embodiments of the present invention.

Since both the ITE processor 50 and the receiver 39 contain signal processing components, specific embodiments vary as to how much processing is performed by each. For example, in a one system using CIS processing, the ITE processor 50 produces a minimally processed analog audio signal for the subcutaneous receiver 39. In other embodiments, the audio signal from the ITE processor 50, while still analog, may have more sophisticated analog signal processing performed on it; for example, automatic gain control (AGC) and beamforming such as is done in a conventional hearing aid. Typical methods for transmitting an analog audio signal include well-known techniques such as amplitude modulation (AM) or frequency modulation (FM). In any case, the receiver 39 processes the received analog audio information using the CIS digital signal processing technique, and produces a stimulation signal for the electrodes of the implanted electrode carrier 46.

But, in an alternative embodiment, the ITE processor 50 also may perform analog to digital conversion of the audio signal, followed by digital signal processing. For instance, the ITE processor 50 may transmit to the receiver 39 a sequence of digital data frames containing the information necessary to reconstruct the analog audio signal. Typical methods for transmitting a digital audio signal include such well-known techniques as amplitude shift keying (ASK), frequency shift keying (FSK), and phase shift keying (PSK). The receiver 39 may then perform CIS processing of the received digital signal and construct an electrode stimulation pattern based on the information in the received digital data signal. Alternatively, the ITE processor 50 may further process the digital audio signal to produce the CIS pulse information, which is then converted into a sequence of digital frames and transmitted to the receiver 39. The receiver 39 then uses the information in the received digital frame sequence to construct the CIS pulse pattern for the implanted electrodes.

Similar shifting of signal processing functionality between the ITE processor 50 and the receiver 39 may be used in other specific embodiments based on other signal processing strategies. Moreover, the information channel to the receiver 39 can be used by other devices than the ITE processor 50. For example, using the rf frequency of the receiver 39 and the proper audio information format, a telephone, television, radio, or other external audio device could transmit an audio signal to the receiver 39.

In representative embodiments, the receiver 39 may contain rechargeable batteries. With such an arrangement, a behind-the-ear (BTE) module may be used at night while the user is sleeping to inductively couple electrical power from primary coil 38 through the skin to secondary coil 34 to recharge the batteries in the receiver 39 while the user is asleep. Then, in the morning, the user can remove the BTE module and rely on the recharged batteries in the receiver 39 to provide electrical power throughout the day to the implanted portion of the system. Alternatively, a rechargeable battery module may be implanted separately from the receiver 39. Using an implanted battery, there is no prominently visible external module, only the unobtrusive ITE processor, which appears to be a conventional hearing aid.

In another alternative embodiment, implanted rechargeable batteries are not used. Rather, the previously known inductive coupling arrangement is used to provide electrical power to the implanted portion of the system. And, if the all the signal processing is performed by the implanted portion of the system, the ITE processor may omitted altogether by also implanting a microphone in communication with the implanted receiver. Thus, power transmission and information transmission and processing are still kept as separate functions transmitted over separate channels. This arrangement allows for a low profile BTE module that may be covered by the user's hair, and which contains just an external battery and the power transmission components. These parts can be made to be very robust and inexpensive, and servicing is greatly simplified.

In another alternative embodiment, an external signal processing module may be added to the external part of the power transmission system. An rf receiver within this module receives and processes the audio information sent by the transmitter in the ITE processor. The processed audio is then modulated into the power transmission signal, which has enough rf-bandwidth to transmit broadband stimulation data.

The foregoing discussion has described various advantages of representative embodiments of the present invention over existing cochlear implant systems that use an external BTE or body-worn processor. It should be noted that the various embodiments also offer significant advantages over fully implanted cochlear implant systems that have no external components. For example, the surgery to place the implanted portions of the system is less complicated than in a fully implanted system that surgically implants a microphone in the ear canal. Also, the location of the microphone in the ITE processor can be acoustically optimized compared to a system that integrates the microphone into the implant package. And, newly emerging signal processing strategies can be readily implemented in the ITE processor as they become available. This is not possible if the processing circuits are fully implanted.

Although various exemplary embodiments of the invention have been disclosed, it should be apparent to those skilled in the art that various changes and modifications can be made which will achieve some of the advantages of the invention without departing from the true scope of the invention.

What is claimed is:

1. A signal processing device for a cochlear implant, the device comprising:
 a device body that fits into the ear canal of a user, the device body containing:
  (i) a microphone that converts an acoustic signal present at the device body into a representative electrical signal;
  (ii) a signal processor that performs signal processing of the representative electrical signal to form a cochlear implant signal; and (iii) a transmitter that converts the cochlear implant signal into a radio signal for transmission to a cochlear implant.

2. A device according to claim 1, wherein the device body further includes:

a mechanical stimulation module that delivers to the inner ear structure of the user a mechanical stimulation signal representative of a portion of the acoustic signal, wherein the cochlear implant signal is representative of a first subrange of frequencies in the acoustic signal, and the mechanical stimulation signal is representative of a second subrange of frequencies in the acoustic signal.

3. A device according to claim 1, wherein the processing performed by the signal processor includes at least one of compression, beamforming, and filtering.

4. A device according to claim 1, wherein the signal processing includes continuous interleaved sampling (CIS) digital signal processing.

5. A device according to claim 1, wherein the signal processing includes channel specific sampling sequences (CSSS).

6. A device according to claim 1, wherein the signal processing includes spectral peak (SPEAK) digital signal processing.

7. A device according to claim 1, wherein the signal processing includes compressed analog (CA) signal processing.

8. A cochlear implant system comprising:

a signal processor that fits in the ear canal of a user and processes an acoustic signal present in the ear of the user to produce a representative radio signal;

a power transmitter that transmits an electrical power signal through the skin of the user; and a cochlear implant that receives the radio signal and the electrical power signal and produces for the auditory nerve of the user an electrical stimulation signal representative of the acoustic signal.

9. A system according to claim 8, wherein the signal processor further includes:

a mechanical stimulation module that delivers to the inner ear structure of the user a mechanical stimulation signal representative of a portion of the acoustic signal, wherein the cochlear implant signal is representative of a first subrange of frequencies in the acoustic signal, and the mechanical stimulation signal is representative of a second subrange of frequencies in the acoustic signal.

10. A system according to claim 8, further comprising:

an implanted battery module that powers the cochlear implant, and that is rechargeable responsive to the transmitted electrical power signal.

11. A system according to claim 8, wherein the processing performed by the signal processor includes at least one of compression, beamforming, and filtering.

12. A system according to claim 8, wherein the processing performed by the signal processor includes continuous interleaved sampling (CIS) digital signal processing.

13. A system according to claim 8, wherein the processing performed by the signal processor includes channel specific sampling sequences (CSSS).

14. A system according to claim 8, wherein the processing performed by the signal processor includes spectral peak (SPEAK) digital signal processing.

15. A system according to claim 8, wherein the processing performed by the signal processor includes compressed analog (CA) signal processing.

16. A system according to claim 8, wherein the cochlear implant uses extracochlear electrodes to deliver the electrical stimulation signal.

17. A system according to claim 8, wherein the cochlear implant uses cochleostomy window associated electrodes to deliver the electrical stimulation signal.

18. A system according to claim 8, wherein the cochlear implant uses multi-channel array electrodes partially inserted into the cochlea of the user to deliver the electrical stimulation signal.

19. A system according to claim 8, wherein the cochlear implant uses multi-channel array electrodes fully inserted into the cochlea of the user to deliver the electrical stimulation signal.

* * * * *

UNITED STATES PATENT AND TRADEMARK OFFICE
CERTIFICATE OF CORRECTION

PATENT NO. : 6,556,870 B2
DATED : April 29, 2003
INVENTOR(S) : Clemens N. Zierhofer, Erwin S. Hochmair and Ingeborg J. Hochmair It is certified that error appears in the above-identified patent and that said Letters Patent is hereby corrected as shown below:

<u>Title page,</u>
Item [75], Inventors, replace "(AU)" with -- (AT) -- (all occurrences).
Item [73], Assingee, replace "Med-El" with -- MED-EL --.

Signed and Sealed this

Fifteenth Day of June, 2004

JON W. DUDAS
*Acting Director of the United States Patent and Trademark Office*